(12) United States Patent
Wei et al.

(10) Patent No.: US 7,662,643 B2
(45) Date of Patent: Feb. 16, 2010

(54) REDUCTION OF THE HOOK EFFECT IN MEMBRANE-BASED ASSAY DEVICES

(75) Inventors: Ning Wei, Roswell, GA (US); Yanbin Huang, Foster City, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/780,671

(22) Filed: Jul. 20, 2007

(65) Prior Publication Data

US 2008/0014659 A1   Jan. 17, 2008

Related U.S. Application Data

(62) Division of application No. 10/325,614, filed on Dec. 19, 2002, now Pat. No. 7,247,500.

(51) Int. Cl.
*G01N 33/53* (2006.01)

(52) U.S. Cl. .................. 436/514; 435/7.1; 435/7.92; 435/288.6; 435/287.1; 436/518; 436/523; 436/805; 436/809; 422/56; 422/57; 422/58; 422/59; 422/61

(58) Field of Classification Search .......... 435/7.1, 435/7.92, 288.6, 287.1; 436/514, 518, 523, 436/805, 809; 422/56–61
See application file for complete search history.

(56) References Cited

U.S. PATENT DOCUMENTS

| 164,659 | A | 5/1875 | Reckhow et al. |
| 1,366,241 | A | 1/1921 | Burch |
| 3,700,623 | A | 10/1972 | Keim |
| 3,772,076 | A | 11/1973 | Keim |
| 4,094,647 | A | 6/1978 | Deutsch et al. |
| 4,110,529 | A | 8/1978 | Stoy |
| 4,115,535 | A | 9/1978 | Giaever |
| 4,168,146 | A | 9/1979 | Grubb et al. |
| RE30,267 | E | 5/1980 | Bruschi |
| 4,210,723 | A | 7/1980 | Dorman et al. |
| 4,235,601 | A | 11/1980 | Deutsch et al. |

(Continued)

FOREIGN PATENT DOCUMENTS

EP   0073593 A1   3/1983

(Continued)

OTHER PUBLICATIONS

Bangs, Leigh B. New developments in Particle-Based Tests and Immunoassays. JIFCC. vol. 2, issue 4, pp. 188-193.*

(Continued)

*Primary Examiner*—Bao-Thuy L Nguyen
(74) *Attorney, Agent, or Firm*—Dority & Manning, P.A.

(57) ABSTRACT

A membrane-based assay device for detecting the presence or quantity of an analyte residing in a test sample is provided. The device utilizes a chromatographic zone on which is disposed a plurality of microporous particles. The chromatographic zone can effectively reduce the "hook effect" in a simple, efficient, and relatively inexpensive manner. In particular, the plurality of microporous particles allows larger-sized analyte/probe complexes to reach the detection zone before the uncomplexed analyte. Because the uncomplexed analyte is substantially inhibited from competing with the complexes for the binding sites at the detection zone, the incidence of "false negatives" may be limited, even at relatively high analyte concentrations.

21 Claims, 5 Drawing Sheets

U.S. PATENT DOCUMENTS

| | | | |
|---|---|---|---|
| 4,275,149 A | 6/1981 | Litman et al. | |
| 4,312,228 A | 1/1982 | Wohltjen | |
| 4,361,537 A | 11/1982 | Deutsch et al. | |
| 4,363,874 A | 12/1982 | Greenquist | |
| 4,366,241 A | 12/1982 | Tom et al. | |
| 4,374,925 A | 2/1983 | Litman et al. | |
| 4,385,126 A | 5/1983 | Chen et al. | |
| 4,426,451 A | 1/1984 | Columbus | |
| 4,427,836 A | 1/1984 | Kowalski et al. | |
| 4,435,504 A | 3/1984 | Zuk et al. | |
| 4,441,373 A | 4/1984 | White | |
| 4,442,204 A | 4/1984 | Greenquist et al. | |
| 4,444,592 A | 4/1984 | Ludwig | |
| 4,477,635 A | 10/1984 | Mitra | |
| 4,480,042 A | 10/1984 | Craig et al. | |
| 4,533,499 A | 8/1985 | Clark et al. | |
| 4,533,629 A | 8/1985 | Litman et al. | |
| 4,534,356 A | 8/1985 | Papadakis | |
| 4,537,657 A | 8/1985 | Keim | |
| 4,537,861 A | 8/1985 | Elings et al. | |
| 4,540,659 A | 9/1985 | Litman et al. | |
| 4,552,458 A | 11/1985 | Lowne | |
| 4,561,286 A | 12/1985 | Sekler et al. | |
| 4,562,157 A | 12/1985 | Lowe et al. | |
| 4,586,695 A | 5/1986 | Miller | |
| 4,595,661 A | 6/1986 | Cragle et al. | |
| 4,596,697 A | 6/1986 | Ballato | |
| 4,614,723 A | 9/1986 | Schmidt et al. | |
| 4,632,559 A | 12/1986 | Brunsting | |
| 4,661,235 A | 4/1987 | Krull et al. | |
| 4,698,262 A | 10/1987 | Schwartz et al. | |
| 4,703,017 A | 10/1987 | Campbell et al. | |
| 4,714,682 A | 12/1987 | Schwartz | |
| 4,722,889 A | 2/1988 | Lee et al. | |
| 4,727,019 A | 2/1988 | Valkirs et al. | |
| 4,731,337 A | 3/1988 | Luotola et al. | |
| 4,743,542 A | 5/1988 | Graham, Jr. et al. | |
| 4,776,944 A | 10/1988 | Janata et al. | |
| 4,837,168 A | 6/1989 | de Jaeger et al. | |
| 4,842,783 A | 6/1989 | Blaylock | |
| 4,843,000 A | 6/1989 | Litman et al. | |
| 4,843,021 A | 6/1989 | Noguchi et al. | |
| 4,844,613 A | 7/1989 | Batchelder et al. | |
| 4,849,338 A | 7/1989 | Litman et al. | |
| 4,855,240 A | 8/1989 | Rosenstein et al. | |
| 4,857,453 A | 8/1989 | Ullman et al. | |
| 4,867,908 A | 9/1989 | Recktenwald et al. | |
| 4,868,126 A | 9/1989 | Schwartz | |
| 4,877,586 A | 10/1989 | Devaney, Jr. et al. | |
| 4,877,747 A | 10/1989 | Stewart | |
| 4,895,017 A | 1/1990 | Pyke et al. | |
| 4,916,056 A | 4/1990 | Brown, III et al. | |
| 4,917,503 A | 4/1990 | Bhattacharjee | |
| 4,940,734 A | 7/1990 | Ley et al. | |
| 4,963,498 A | 10/1990 | Hillman et al. | |
| 4,973,670 A | 11/1990 | McDonald et al. | |
| 4,992,385 A | 2/1991 | Godfrey | |
| 5,003,178 A | 3/1991 | Livesay | |
| 5,023,053 A | 6/1991 | Finlan | |
| 5,026,653 A | 6/1991 | Lee et al. | |
| 5,035,863 A | 7/1991 | Finlan et al. | |
| 5,055,265 A | 10/1991 | Finlan | |
| 5,063,081 A | 11/1991 | Cozzette et al. | |
| 5,064,619 A | 11/1991 | Finlan | |
| 5,075,077 A | 12/1991 | Durley, III et al. | |
| 5,076,094 A | 12/1991 | Frye et al. | |
| 5,096,671 A | 3/1992 | Kane et al. | |
| 5,100,238 A | 3/1992 | Nailor et al. | |
| 5,114,676 A | 5/1992 | Leiner et al. | |
| 5,120,662 A | 6/1992 | Chan et al. | |
| 5,124,254 A | 6/1992 | Hewlins et al. | |
| 5,134,057 A | 7/1992 | Kuypers et al. | |
| 5,137,609 A | 8/1992 | Manian et al. | |
| 5,143,854 A | 9/1992 | Pirrung et al. | |
| 5,145,784 A | 9/1992 | Cox et al. | |
| 5,152,758 A | 10/1992 | Kaetsu et al. | |
| 5,156,953 A | 10/1992 | Litman et al. | |
| 5,182,135 A | 1/1993 | Giesecke et al. | |
| 5,196,350 A | 3/1993 | Backman et al. | |
| 5,200,084 A | 4/1993 | Liberti et al. | |
| 5,208,535 A | 5/1993 | Nakayama et al. | |
| 5,221,454 A | 6/1993 | Manian et al. | |
| 5,225,935 A | 7/1993 | Watanabe et al. | |
| 5,234,813 A | 8/1993 | McGeehan et al. | |
| 5,235,238 A | 8/1993 | Nomura et al. | |
| 5,238,815 A | 8/1993 | Higo et al. | |
| 5,242,828 A | 9/1993 | Bergström et al. | |
| 5,252,459 A | 10/1993 | Tarcha et al. | |
| 5,262,299 A | 11/1993 | Evangelista et al. | |
| 5,268,306 A | 12/1993 | Berger et al. | |
| 5,314,923 A | 5/1994 | Cooke et al. | |
| 5,316,727 A | 5/1994 | Suzuki et al. | |
| 5,320,944 A | 6/1994 | Okada et al. | |
| 5,321,492 A | 6/1994 | Detwiler et al. | |
| 5,327,225 A | 7/1994 | Bender et al. | |
| 5,330,898 A | 7/1994 | Bar-Or et al. | |
| 5,342,759 A | 8/1994 | Litman et al. | |
| 5,352,582 A | 10/1994 | Lichtenwalter et al. | |
| 5,356,782 A | 10/1994 | Moorman et al. | |
| 5,358,852 A | 10/1994 | Wu | |
| 5,369,717 A | 11/1994 | Attridge | |
| 5,374,531 A | 12/1994 | Jensen | |
| 5,374,563 A | 12/1994 | Maule | |
| 5,376,255 A | 12/1994 | Gumbrecht et al. | |
| 5,387,503 A | 2/1995 | Selmer et al. | |
| 5,395,754 A | 3/1995 | Lambotte et al. | |
| 5,415,842 A | 5/1995 | Maule | |
| 5,418,136 A | 5/1995 | Miller et al. | |
| 5,424,219 A | 6/1995 | Jirikowski | |
| 5,432,057 A | 7/1995 | Litman et al. | |
| 5,436,161 A | 7/1995 | Bergström et al. | |
| 5,445,971 A | 8/1995 | Rohr | |
| 5,451,683 A | 9/1995 | Barrett et al. | |
| 5,455,475 A | 10/1995 | Josse et al. | |
| 5,464,741 A | 11/1995 | Hendrix | |
| 5,466,574 A | 11/1995 | Liberti et al. | |
| 5,467,778 A | 11/1995 | Catt et al. | |
| 5,468,606 A | 11/1995 | Bogart et al. | |
| 5,482,830 A | 1/1996 | Bogart et al. | |
| 5,482,867 A | 1/1996 | Barrett et al. | |
| 5,484,867 A | 1/1996 | Lichtenham et al. | |
| 5,489,678 A | 2/1996 | Fodor et al. | |
| 5,489,988 A | 2/1996 | Ackley et al. | |
| 5,492,840 A | 2/1996 | Malmqvist et al. | |
| 5,500,350 A | 3/1996 | Baker et al. | |
| 5,504,013 A | 4/1996 | Senior | |
| 5,508,171 A | 4/1996 | Walling et al. | |
| 5,510,481 A | 4/1996 | Bednarski et al. | |
| 5,512,131 A | 4/1996 | Kumar et al. | |
| 5,514,559 A | 5/1996 | Markert-Hahn et al. | |
| 5,514,785 A | 5/1996 | Van Ness et al. | |
| 5,516,635 A | 5/1996 | Ekins et al. | |
| 5,518,689 A | 5/1996 | Dosmann et al. | |
| 5,518,883 A | 5/1996 | Soini | |
| 5,527,711 A | 6/1996 | Tom-Moy et al. | |
| 5,534,132 A | 7/1996 | Vreeke et al. | |
| 5,554,541 A | 9/1996 | Malmqvist et al. | |
| 5,559,041 A * | 9/1996 | Kang et al. | 436/518 |
| 5,569,608 A | 10/1996 | Sommer | |
| 5,571,684 A | 11/1996 | Lawrence et al. | |
| 5,573,909 A | 11/1996 | Singer et al. | |
| 5,585,279 A | 12/1996 | Davidson | |
| 5,589,401 A | 12/1996 | Hansen et al. | |
| 5,591,581 A | 1/1997 | Massey et al. | |

| | | | | | |
|---|---|---|---|---|---|
| 5,596,414 A | 1/1997 | Tyler | 6,255,066 B1 | 7/2001 | Louderback |
| 5,599,668 A | 2/1997 | Stimpson et al. | 6,261,779 B1 | 7/2001 | Barbera-Guillem et al. |
| 5,618,888 A | 4/1997 | Choi et al. | 6,268,222 B1 | 7/2001 | Chandler et al. |
| 5,620,850 A | 4/1997 | Bamdad et al. | 6,270,637 B1 | 8/2001 | Crismore et al. |
| 5,637,509 A | 6/1997 | Hemmilä et al. | 6,271,040 B1 | 8/2001 | Buechler |
| 5,647,994 A | 7/1997 | Tuunanen et al. | 6,281,006 B1 | 8/2001 | Heller et al. |
| 5,658,443 A | 8/1997 | Yamamoto et al. | 6,284,472 B1 | 9/2001 | Wei et al. |
| 5,663,213 A | 9/1997 | Jones et al. | 6,287,783 B1 | 9/2001 | Maynard et al. |
| 5,670,381 A | 9/1997 | Jou et al. | 6,287,871 B1 | 9/2001 | Herron et al. |
| 5,672,256 A | 9/1997 | Yee | 6,294,392 B1 | 9/2001 | Kuhr et al. |
| 5,700,636 A | 12/1997 | Sheiness et al. | 6,306,665 B1 | 10/2001 | Buck et al. |
| 5,726,064 A | 3/1998 | Robinson et al. | D450,854 S | 11/2001 | Lipman et al. |
| 5,731,147 A | 3/1998 | Bard et al. | 6,331,438 B1 | 12/2001 | Aylott et al. |
| 5,736,188 A | 4/1998 | Alcock et al. | 6,348,186 B1 | 2/2002 | Sutton et al. |
| 5,753,517 A | 5/1998 | Brooks et al. | 6,362,011 B1 | 3/2002 | Massey et al. |
| 5,770,416 A | 6/1998 | Lihme et al. | 6,368,873 B1 | 4/2002 | Chang et al. |
| 5,780,308 A | 7/1998 | Ching et al. | 6,368,875 B1 | 4/2002 | Geisberg |
| 5,795,470 A | 8/1998 | Wang et al. | 6,387,707 B1 | 5/2002 | Seul et al. |
| 5,795,543 A | 8/1998 | Poto et al. | 6,391,558 B1 | 5/2002 | Henkens et al. |
| 5,811,526 A | 9/1998 | Davidson | 6,399,295 B1 | 6/2002 | Kaylor et al. |
| 5,827,748 A | 10/1998 | Golden | 6,399,397 B1 | 6/2002 | Zarling et al. |
| 5,834,226 A | 11/1998 | Maupin | 6,403,384 B1 * | 6/2002 | Lea ............................ 436/518 |
| 5,837,429 A | 11/1998 | Nohr et al. | 6,407,492 B1 | 6/2002 | Avnery et al. |
| 5,837,546 A | 11/1998 | Allen et al. | 6,411,439 B2 | 6/2002 | Nishikawa |
| 5,837,547 A | 11/1998 | Schwartz | 6,413,410 B1 | 7/2002 | Hodges et al. |
| 5,843,692 A | 12/1998 | Phillips et al. | 6,436,651 B1 | 8/2002 | Everhart et al. |
| 5,852,229 A | 12/1998 | Josse et al. | 6,436,722 B1 | 8/2002 | Clark et al. |
| 5,876,944 A | 3/1999 | Kuo | 6,444,423 B1 | 9/2002 | Meade et al. |
| 5,885,527 A | 3/1999 | Buechler | 6,448,091 B1 | 9/2002 | Massey et al. |
| 5,906,921 A | 5/1999 | Ikeda et al. | 6,451,607 B1 | 9/2002 | Lawrence et al. |
| 5,910,447 A | 6/1999 | Lawrence et al. | 6,455,861 B1 | 9/2002 | Hoyt |
| 5,910,940 A | 6/1999 | Guerra | 6,461,496 B1 | 10/2002 | Feldman et al. |
| 5,922,537 A | 7/1999 | Ewart et al. | 6,468,741 B1 | 10/2002 | Massey et al. |
| 5,922,550 A | 7/1999 | Everhart et al. | 6,472,226 B1 | 10/2002 | Barradine et al. |
| 5,951,492 A | 9/1999 | Douglas et al. | 6,479,146 B1 | 11/2002 | Caruso et al. |
| 5,962,995 A | 10/1999 | Avnery | 6,509,085 B1 | 1/2003 | Kennedy |
| 6,004,530 A | 12/1999 | Sagner et al. | 6,509,196 B1 | 1/2003 | Brooks et al. |
| 6,020,047 A | 2/2000 | Everhart | 6,511,814 B1 | 1/2003 | Carpenter |
| 6,027,904 A | 2/2000 | Devine et al. | 6,556,299 B1 | 4/2003 | Rushbrooke et al. |
| 6,027,944 A | 2/2000 | Robinson et al. | 6,566,508 B2 | 5/2003 | Bentsen et al. |
| 6,030,792 A | 2/2000 | Otterness et al. | 6,573,040 B2 | 6/2003 | Everhart et al. |
| 6,030,840 A | 2/2000 | Mullinax et al. | 6,579,673 B2 | 6/2003 | McGrath et al. |
| 6,033,574 A | 3/2000 | Siddiqi | 6,582,930 B1 | 6/2003 | Ponomarev et al. |
| 6,048,623 A | 4/2000 | Everhart et al. | 6,585,939 B1 | 7/2003 | Dapprich |
| 6,060,256 A | 5/2000 | Everhart et al. | 6,613,583 B1 | 9/2003 | Richter et al. |
| 6,080,391 A | 6/2000 | Tsuchiya et al. | 6,617,488 B1 | 9/2003 | Springer et al. |
| 6,084,683 A | 7/2000 | Bruno et al. | 6,670,115 B1 | 12/2003 | Zhang |
| 6,087,184 A | 7/2000 | Magginetti et al. | 6,696,304 B1 | 2/2004 | Davies |
| 6,099,484 A | 8/2000 | Douglas et al. | 6,720,007 B2 | 4/2004 | Walt et al. |
| 6,103,537 A | 8/2000 | Ullman et al. | 6,787,368 B1 | 9/2004 | Wong et al. |
| 6,117,090 A | 9/2000 | Caillouette | 6,815,218 B1 | 11/2004 | Jacobson et al. |
| 6,136,549 A | 10/2000 | Feistel | 7,247,500 B2 | 7/2007 | Wei et al. |
| 6,136,611 A | 10/2000 | Saaski et al. | 2001/0055776 A1 | 12/2001 | Greenwalt |
| 6,139,961 A | 10/2000 | Blankenship et al. | 2002/0070128 A1 | 6/2002 | Beckmann |
| 6,151,110 A | 11/2000 | Markart | 2002/0146754 A1 | 10/2002 | Kitawaki et al. |
| 6,165,798 A | 12/2000 | Brooks | 2002/0164659 A1 | 11/2002 | Rao et al. |
| 6,171,780 B1 | 1/2001 | Pham et al. | 2003/0017615 A1 | 1/2003 | Sidwell et al. |
| 6,171,870 B1 | 1/2001 | Freitag | 2003/0119202 A1 | 6/2003 | Kaylor et al. |
| 6,174,646 B1 | 1/2001 | Hirai et al. | 2003/0119204 A1 | 6/2003 | Wei et al. |
| 6,177,281 B1 | 1/2001 | Manita | 2003/0124739 A1 | 7/2003 | Song et al. |
| 6,180,288 B1 | 1/2001 | Everhart et al. | 2003/0178309 A1 | 9/2003 | Huang et al. |
| 6,183,972 B1 | 2/2001 | Kuo et al. | 2004/0014073 A1 | 1/2004 | Trau et al. |
| 6,184,042 B1 | 2/2001 | Neumann et al. | 2004/0043502 A1 | 3/2004 | Song et al. |
| 6,194,220 B1 | 2/2001 | Malick et al. | 2004/0043507 A1 | 3/2004 | Song et al. |
| 6,200,820 B1 | 3/2001 | Hansen et al. | 2004/0043511 A1 | 3/2004 | Song et al. |
| 6,221,238 B1 | 4/2001 | Grundig et al. | 2004/0043512 A1 | 3/2004 | Song et al. |
| 6,221,579 B1 | 4/2001 | Everhart et al. | 2004/0106190 A1 | 6/2004 | Yang et al. |
| 6,234,974 B1 | 5/2001 | Catt et al. | 2004/0121334 A1 | 6/2004 | Wei et al. |
| 6,235,241 B1 | 5/2001 | Catt et al. | 2004/0197819 A1 | 10/2004 | Yang et al. |
| 6,235,471 B1 | 5/2001 | Knapp et al. | 2005/0112703 A1 | 5/2005 | Song |
| 6,235,491 B1 | 5/2001 | Connolly | 2005/0112779 A1 | 5/2005 | Wei et al. |
| 6,241,863 B1 | 6/2001 | Monbouquette | 2005/0112780 A1 | 5/2005 | Song |
| 6,242,268 B1 | 6/2001 | Wieder et al. | 2005/0136500 A1 | 6/2005 | Yang et al. |

| | | | |
|---|---|---|---|
| 2005/0136529 | A1 | 6/2005 | Yang et al. |
| 2005/0136550 | A1 | 6/2005 | Yang et al. |
| 2005/0191704 | A1 | 9/2005 | Boga et al. |
| 2005/0244953 | A1 | 11/2005 | Cohen |

FOREIGN PATENT DOCUMENTS

| | | | |
|---|---|---|---|
| EP | 0205698 | A1 | 12/1986 |
| EP | 0420053 | A1 | 4/1991 |
| EP | 0437287 | B1 | 7/1991 |
| EP | 0462376 | B1 | 12/1991 |
| EP | 0469377 | A2 | 2/1992 |
| EP | 0539035 | A2 | 4/1993 |
| EP | 0539035 | B1 | 4/1993 |
| EP | 0617285 | A2 | 9/1994 |
| EP | 0617285 | A3 | 9/1994 |
| EP | 0657737 | A2 | 6/1995 |
| EP | 0657737 | A3 | 6/1995 |
| EP | 0660114 | B1 | 6/1995 |
| EP | 0703454 | A1 | 3/1996 |
| EP | 0711414 | B1 | 5/1996 |
| EP | 0724156 | A1 | 7/1996 |
| EP | 0745843 | A2 | 12/1996 |
| EP | 0745843 | A3 | 12/1996 |
| EP | 0833159 | A2 | 4/1998 |
| EP | 0859230 | A1 | 8/1998 |
| EP | 0898169 | B1 | 2/1999 |
| EP | 1221616 | A1 | 7/2002 |
| GB | 2273772 | A | 6/1994 |
| WO | WO 8804777 | A1 | 6/1988 |
| WO | WO 9005305 | A1 | 5/1990 |
| WO | WO 9105999 | A2 | 5/1991 |
| WO | WO 9221769 | A1 | 12/1992 |
| WO | WO 9221770 | A1 | 12/1992 |
| WO | WO 9221975 | A1 | 12/1992 |
| WO | WO 9301308 | A1 | 1/1993 |
| WO | WO 9319370 | A1 | 9/1993 |
| WO | WO 9406012 | A1 | 3/1994 |
| WO | WO 9413835 | A1 | 6/1994 |
| WO | WO 9415193 | A1 | 7/1994 |
| WO | WO 9626435 | A1 | 8/1996 |
| WO | WO 9703347 | A1 | 1/1997 |
| WO | WO 9709620 | A1 | 3/1997 |
| WO | WO 9737222 | A1 | 10/1997 |
| WO | WO 9810334 | A1 | 3/1998 |
| WO | WO 9815831 | A1 | 4/1998 |
| WO | WO 9827417 | A1 | 6/1998 |
| WO | WO 9843086 | A1 | 10/1998 |
| WO | WO 9910742 | A1 | 3/1999 |
| WO | WO 9930131 | A1 | 6/1999 |
| WO | WO 9936777 | A1 | 7/1999 |
| WO | WO 9964864 | A1 | 12/1999 |
| WO | WO 0019199 | A1 | 4/2000 |
| WO | WO 0023805 | A1 | 4/2000 |
| WO | WO 0034781 | A1 | 6/2000 |
| WO | WO 0036416 | A1 | 6/2000 |
| WO | WO 0046839 | A2 | 8/2000 |
| WO | WO 0046839 | A3 | 8/2000 |
| WO | WO 0047983 | A1 | 8/2000 |
| WO | WO 0050891 | A1 | 8/2000 |
| WO | WO 0078917 | A1 | 12/2000 |
| WO | WO 0129559 | A1 | 4/2001 |
| WO | WO 0138873 | A2 | 5/2001 |
| WO | WO 0150129 | A2 | 7/2001 |
| WO | WO 0150129 | A3 | 7/2001 |
| WO | WO 0163299 | A1 | 8/2001 |
| WO | WO 0171344 | A2 | 9/2001 |
| WO | WO 0198765 | A1 | 12/2001 |
| WO | WO 0198785 | A2 | 12/2001 |
| WO | WO 02077646 | A1 | 10/2002 |
| WO | WO 03005013 | A1 | 1/2003 |
| WO | WO 03058246 | A1 | 7/2003 |

OTHER PUBLICATIONS

8 Photographs of Accu-chek® Blood Glucose Meter.
Abstract of DE10024145A1, Nov. 22, 2001.
Abstract of Japanese Patent No. JP 8062214, Mar. 8, 1996.
*AMI Screen Printers*—Product Information, 4 pages.
Article—*A conductometral biosensor for biosecurity*, Zarini Muhammad-Tahir and Evangelyn C. Alocilja, Biosensors & Bioelectronics, vol. 18, 2003, pp. 813-819.
Article—*A Disposable Amperometric Sensor Screen Printed on a Nitrocellulose Strip: A Glucose Biosensor Employing Lead Oxide as an Interference-Removing Agent*, Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.
Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.
Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.
Article—*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp. 4247-4249.
Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.
Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.
Article—*Analysis of electrical equivalent circuit of quartz crystal resonator loaded with viscous conductive liquids*, Journal of Electroanalytical Chemistry, vol. 379, 1994, pp. 21-33.
Article—*Application of rod-like polymers with ionophores as Langmuir-Blodgett membranes for Si-based ion sensors*, Sensors and Actuators B, 1992, pp. 211-216.
Article—*Attempts of Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.
Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.
Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.
Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.
Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.
Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.
Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.
Article—*Fabrication of Patterned, Electrically Conducting Polypyrrole Using a Self-Assembled Monolayer: A Route to All-Organic*

*Circuits*, Christopher B. Gorman, Hans A. Biebuyck, and George M. Whitesides, American Chemical Society, 2 pages, 1994.

Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.

Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.

Article—*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.

Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.

Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

Article—*Hollow latex particles: synthesis and applications*, Charles J. McDonald and Michael J. Devon, Advances in Colloid and Interface Science, Vo. 99, 2002, pp. 181-213.

Article—*How to Build a Spectrofluorometer*, Spex Fluorolog 3, Horiba Group, pp. 1-14.

Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.

Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.

Article—*Inert Phosphorescent Nanospheres as Markers for Optical Assays*, Jens M. Kürner, Ingo Klimant, Christian Krause, Harald Preu, Werner Kunz, and Otto S. Wolfbeis, Bioconjugate Chem., vol. 12, No. 6, 2001, pp. 883-889.

Article—*Intelligent Gels*, Yoshihito Osada and Simon B. Ross-Murphy, Scientific American, May 1993, pp. 82-87.

Article—*Latex Immunoassays*, Leigh B. Bangs, Journal of Clinical Immunoassay, vol. 13, No. 3, 1990, pp. 127-131.

Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.

Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.

Article—*Microfabrication by Microcontact Printing Of Self-Assembled Monolyaers*, James L. Wilbur, Armit Kumar, Enoch Kim, and George M. Whitesides, Advanced Materials, vol. 6, No. 7/8, 1994, pp. 600-604.

Article—*Modification of monoclonal and polyclonal IgG with palladium (II) coproporphyrin I: stimulatory and inhibitory functional effects induced by two different methods*, Sergey P. Martsev, Valery A. Preygerzon, Yanina I. Mel'nikova, Zinaida I. Ksavchuk, Gely V. Ponomarev, Vitaly E. Lunev, and Alexander P. Savitsky, Journal of Immunological Methods 186, 1996, pp. 293-304.

Article—*Molecular Design Temperature-Responsive Polymers as Intelligent Materials*, Teruo Okano, Advances in Polymer Science, pp. 179-197, 1992.

Article—*Molecular Gradients of w-Substituted Alkanethiols on Gold: Preparation and Characterization*, Bo Liedberg and Pentti Tengvall, Langmuir, vol. 11, No. 10, 1995, pp. 3821-3827.

Article—*Monofunctional Derivatives of Coproporphyrins for Phosphorescent Labeling of Proteins and Binding Assays*, Tomás C. O'Riordan, Aleksi E. Soini, and Dmitri B. Papkovsky, Analytical Biochemistry, vol. 290, 2001, pp. 366-375.

Article—*Near Infrared Phosphorescent Metalloporphrins*, Alexander P. Savitsky Anna V. Savitskaja, Eugeny A. Lukjanetz, Svetlana N. Dashkevich, and Elena A. Makarova, SPIE, vol. 2980, pp. 352-357.

Article—*New Approach to Producing Patterned Biomolecular Assemblies*, Suresh K. Bhatia, James J. Hickman, and Frances S. Ligler, J. Am. Chem. Soc., vol. 114, 1992, pp. 4433-4434.

Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.

Article—*On the use of Zx-LiNbO₃ acoustic plate mode devices as detectors for dilute electrolytes*, F. Josse, Z. A. Shana, D. T. Haworth, and S. Liew, Sensors and Actuators B, vol. 9, 1992, pp. 92-112.

Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkeä, Kaj Blomberg, Tom Palenius, and Kim Pettersson, Clinical Chemistry 42:8, 1996, pp. 1196-1201.

Article—*Optical Biosensor Assay (OBA ™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.

Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.

Article—*Orientation dependence of surface segregation in a dilute Ni-Au alloy*, W. C. Johnson, N. G. Chavka, R. Ku, J. L. Bomback, and P. P. Wynblatt, J. Vac. Sci. Technol. vol. 15, No. 2, Mar./Apr. 1978, pp. 467-469.

Article—*Patterned Condensation Figures as Optical Diffraction Gratings*, Amit Kumar and George M. Whitesides, Science, vol. 263, Jan. 7, 1994, pp. 60-62.

Article—*Patterned Functionalization of Gold and Single Crystal Silicon via Photochemical Reaction of Surface-Confined Derivatives of $(\eta^5-C_5H_5)Mn(CO)_3$*, Doris Kang and Mark S. Wrighton, Langmuir, vol. 7, No. 10, 1991, pp. 2169-2174.

Article—*Patterned Metal Electrodeposition Using an Alkanethiolate Mask*, T. P. Moffat and H. Yang, J. Electrochem. Soc., vol. 142, No. 11, Nov. 1995, pp. L220-L222.

Article—*Performance Evaluation of the Phosphorescent Porphyrin Label: Solid-Phase Immunoassay of α-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.

Article—*Phosphorescent porphyrin probes in biosensors and sensitive bioassays*, D. B. Papkovsky, T. O'Riordan, and A. Soini, Biochemical Society Transactions, Vol. 28, part 2, 2000, pp. 74-77.

Article—*Photolithography of self-assembled monolayers: optimization of protecting groups by an electroanalytical method*, Jamila Jennane, Tanya Boutrous, and Richard Giasson, Can. J. Chem., vol. 74, 1996, pp. 2509-2517.

Article—*Photopatterning and Selective Electroless Metallization of Surface-Attached Ligands*, Walter J. Dressick, Charles S. Dulcey, Jacque H. Georger, Jr., and Jeffrey M. Calvert, American Chemical Society, 2 pages, 1992.

Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.

Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.

Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.

Article—*Principle and Applications of Size-Exclusion Chromatography*, Impact Analytical, pp. 1-3.

Article—*Probing of strong and weak electrolytes with acoustic wave fields*, R. Dahint, D. Grunze, F. Josse, and J. C. Andle, Sensors and Actuators B, vol. 9, 1992, pp. 155-162.

Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.

Article—*Quantitative Prediction of Surface Segregation*, M. P. Seah, Journal of Catalysts, vol. 57, 1979, pp. 450-457.

Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.

Article—*Responsive Gels: Volume Transitions I*, M. Ilavský, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 9 pages, 1993.

Article—*Room-Temperature Phosphorescent Palladium—Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.

Article—*Self-Assembled Monolayer Films for Nanofabrication*, Elizabeth A. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.

Article—*Sensing liquid properties with thickness-shear mode resonators*, S. J. Martin, G. C. Frye, and K. O. Wessendorf, Sensors and Actuators A, vol. 44, 1994, pp. 209-218.

Article—*Separation-Free Sandwich Enzyme Immunoassays Using Microporous Gold Electrodes and Self-Assembled Monolayer/Immobilized Capture Antibodies*, Chuanming Duan and Mark E. Meyerhoff, Analytical Chemistry, vol. 66, No. 9, May 1, 1994, pp. 1369-1377.

Article—*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

Article—*Stimuli-Responsive Poly(N-isopropylacrylamide) Photo- and Chemical-Induced Phase Transitions*, Advances in Polymer Science, pp. 50-65, 1992.

Article—*The Adsorptive Characteristics of Proteins for Polystyrene and Their Significance in Solid-Phase Immunoassays*, L. A. Cantaero, J. E. Butler, and J. W. Osborne, Analytical Biochemistry, vol. 105, 1980, pp. 375-382.

Article—*The Use of Self-Assembled Monolayers and a Selective Etch to Generate Patterned Gold Features*, Amit Kumar, Hans A. Biebuyck, Nicholas L. Abbott, and George M. Whitesides, Journal of the American Chemical Society, vol. 114, 1992, 2 pages.

Article—*Volume Phase Transition of N-Alkylacrylamide Gels*, S. Saito, M. Konno, and H. Inomata, Advances in Polymer Science, vol. 109, 1992, pp. 207-232.

Article—*Whole Blood Capcellia CD4/CD8 Immunoassay for Enumeration of CD4+ and CD8+ Peripheral T Lymphocytes*, Dominique Carrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.

CELQUAT® SC-230M (28-6830), CELQUAT® SC-240C and SC-230M, from National Starch & Chemical, 1 page, 2001.

CELQUAT® SC-230M (28-6830), Polyquaternium-10, from National Starch & Chemical, 1 page, 2001,.

*Dualite® Polymeric Microspheres*, from Pierce & Stevens Corp. a subsidiary of Sovereign Specialty Chemicals, Inc., 2 pages, 2001.

*Dynabeads® Biomagnetic Separation Technology—The Principle* from Dynal Biotech, 2 pages.

*ECCOSPHERES® glass microspheres—hollow glass microspheres* from Emerson & Cuming Composite Materials, Inc., 1 page.

*Factors influencing the formation of hollow ceramic microspheres by water extraction of colloidal droplets*, J. Mater. Res., vol. 10, No. 1, p. 84, Oct. 1994.

*Flow-Based Microimmunoassay*, Analytical Chemistry, vol. 73, No. 24, Mark A. Hayes, Nolan A. Polson, Allison, N. Phayre, and Antonia A. Garcia, Dec. 15, 2001, pp. 5896-5902.

*Fluorescent Microsphere Standards for Flow Cytometry and Fluorescence Microscopy* from Molecular Probes, pp.1-8.

*FluoSpheres® Fluorescent Microspheres*, Production Information from Molecular Probes, Mar. 13, 2001, pp. 1-6.

*Magnetic Microparticles*, Polysciences, Inc. Technical Data Sheet 438, 2 pages.

*Making sun exposure safer for everyone* from Rohm and Haas Company (Bristol Complex), 2 pages.

*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.

Pamphlet—The ClearPlan® Easy Fertility Monitor, 2001.

PCT Search Report and Written Opinion for PCT/US2004/006412, Sep. 28, 2004.

PCT Search Report and Written Opinion for PCT/US2004/006414, Sep. 28, 2004.

PCT Search Report and Written Opinion for PCT/US2004/013180, Aug. 17, 2004.

PCT Search Report for PCT/US02/37653, Apr. 7, 2004.

PCT Search Report for PCT/US03/28628, Mar. 18, 2004.

PCT Search Report for PCT/US03/34543, Apr. 6, 2004.

PCT Search Report for PCT/US03/34544, Apr. 20, 2004.

*POSS Polymer Systems* from Hybrid Plastics, 3 pages.

*The colloidal state*, Introduction to Colloid and Surface Chemistry, 4th Ed., 17 pages.

*Working With FluoSpheres® Fluorescent Microspheres*, Properties and Modifications, Production Information from Molecular Probes, Mar. 9, 2001, pp. 1-5.

* cited by examiner

REDUCTION OF THE HOOK EFFECT IN MEMBRANE-BASED ASSAY DEVICES

RELATED APPLICATIONS

The present application is a divisional of U.S. application Ser. No. 10/325,614, filed on Dec. 19, 2002, which is incorporated herein in its entirety by reference thereto.

BACKGROUND OF THE INVENTION

Various analytical procedures and devices are commonly employed in flow-through assays to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that can be used to determine the presence or concentration of that particular antigen in a biological sample.

There are several well-known immunoassay methods that use immunoreactants labeled with a detectable component so that the analyte can be detected analytically. For example, "sandwich-type" assays typically involve mixing the test sample with detectable probes, such as dyed latex or a radioisotope, which are conjugated with a specific binding member for the analyte. The conjugated probes form complexes with the analyte. These complexes then reach a zone of immobilized antibodies where binding occurs between the antibodies and the analyte to form ternary "sandwich complexes." The sandwich complexes are localized at the zone for detection of the analyte. This technique can be used to obtain quantitative or semi-quantitative results. Some examples of such sandwich-type assays are described in by U.S. Pat. Nos. 4,168,146 to Grubb, et al. and 4,366,241 to Tom, et al.

However, many conventional "sandwich-type" assay formats encounter significant inaccuracies when exposed to relatively high analyte concentrations. Specifically, when the analyte is present at high concentrations, a substantial portion of the analyte in the test sample may not form complexes with the conjugated probes. Thus, upon reaching the detection zone, the uncomplexed analyte competes with the complexed analyte for binding sites. Because the uncomplexed analyte is not labeled with a probe, it cannot be detected. Consequently, if a significant number of the binding sites become occupied by the uncomplexed analyte, the assay may exhibit a "false negative." This problem is commonly referred to as the "hook effect."

Various techniques for reducing the "hook effect" in immunoassays have been proposed. For instance, U.S. Pat. No. 6,184,042 to Neumann, et al. describes one technique for reducing the hook effect in a sandwich assay. The technique involves incubating the sample in the presence of a solid phase with at least two receptors capable of binding to the analyte. The first receptor is an oligomer of a binding molecule selected from antibodies, antibody fragments and mixtures thereof. The second receptor is bound to or capable of being bound to a solid phase. The use of a soluble oligomeric antibody is said to reduce the "hook effect."

A need still exists, however, for an improved technique of reducing the "hook effect" in a simple, efficient, and relatively inexpensive manner.

SUMMARY OF THE INVENTION

In accordance with one embodiment of the present invention, a flow-through assay device for detecting the presence or quantity of an analyte residing in a test sample is disclosed. The flow-through assay device comprises a porous membrane that is in communication with conjugated detection probes capable of generating a detection signal. The porous membrane defines a chromatographic zone within which a plurality of microporous particles are immobilized. The microporous particles can define a plurality of spaces therebetween, the spaces having an average size that is greater than the average size of the micropores. In some embodiments, the average size of the micropores is at least about 100%, in some embodiments at least about 150%, and in some embodiments, at least about 250% less than the average sizes of the spaces. The microporous particles may be selected from the group consisting of polystyrenes, polyacrylamides, polyacrylonitriles; silica beads, and combinations thereof, and the surface thereof may be chemically inert to the analyte.

The porous membrane further defines a detection zone located downstream from the chromatographic zone. A capture reagent is immobilized within the detection zone that is configured to bind to the conjugated detection probes. The conjugated detection probes are capable of generating a detection signal while within the detection zone, wherein the amount of the analyte within the test sample is determined from said detection signal.

In accordance with another embodiment of the present invention, a flow-through, sandwich assay device for detecting the presence or quantity of an analyte residing in a test sample is disclosed. The assay device comprises a porous membrane that is in communication with conjugated detection probes capable of generating a detection signal. The conjugated detection probes are configured to combine with the analyte in the test sample when contacted therewith such that analyte/probe complexes and uncomplexed analyte are formed. The porous membrane defines a chromatographic zone within which a plurality of microporous particles are immobilized. The microporous particles are configured so that the uncomplexed analyte flows through the chromatographic zone at a slower rate than the analyte/probe complexes. The porous membrane further comprises a detection zone located downstream from the chromatographic zone. A capture reagent is immobilized within the detection zone that is configured to bind to the analyte/probe complexes so that the complexes generate a detection signal while within the detection zone, wherein the amount of the analyte within the test sample is determined from the detection signal.

A method for detecting the presence or quantity of an analyte residing in a test sample is disclosed. The method comprises:

i) providing a flow-through assay device comprising a porous membrane, the porous membrane being in communication with conjugated detection probes capable of generating a detection signal, the porous membrane defining a chromatographic zone within which a plurality of microporous particles are immobilized and a detection zone located downstream from the chromatographic zone, wherein a capture reagent is immobilized within the detection zone;

ii) contacting a test sample containing the analyte with the conjugated detection probes so that analyte/probe complexes and uncomplexed analyte are formed; and iii) allowing the analyte/probe complexes and the uncomplexed analyte to reach the chromatographic zone and then the detection zone, wherein the analyte/probe complexes reach the detection zone before the uncomplexed analyte.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
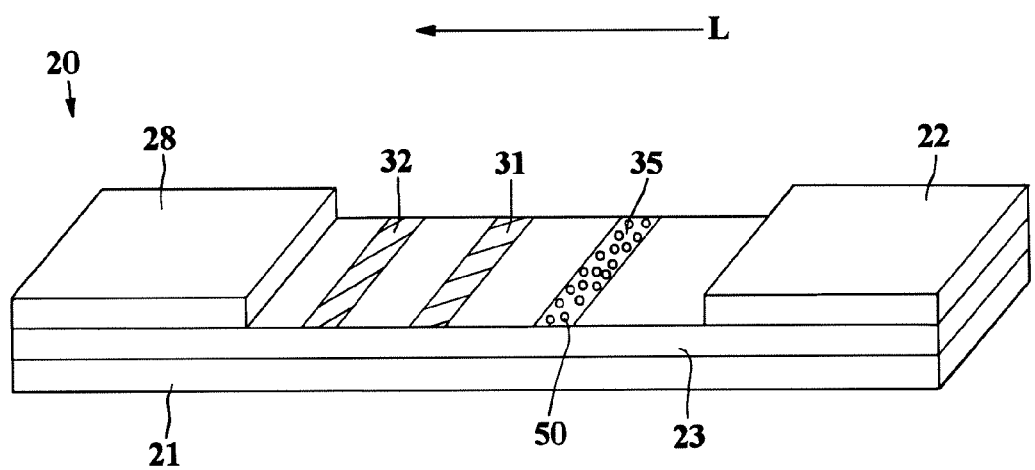
FIG. 1 is a perspective view of one embodiment of a flow-through assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes can include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; C-reactive protein; lipocalins; IgE antibodies; vitamin B2 micro-globulin; glycated hemoglobin (Gly. Hb); cortisol; digitoxin; N-acetylprocainamide 4 (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. Nos. 6,436,651 to Everhart, et al. and 4,366,241 to Tom et al.

As used herein, the term "test sample" generally refers to a material suspected of containing the analyte. The test sample can be used directly as obtained from the source or following a pretreatment to modify the character of the sample. The test sample can be derived from any biological source, such as a physiological fluid, including, blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The test sample can be pretreated prior to use, such as preparing plasma from blood, diluting viscous fluids, and the like. Methods of treatment can involve filtration, precipitation, dilution, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

In general, the present invention is directed to a membrane-based assay device for detecting the presence or quantity of an analyte residing in a test sample. The device utilizes a chromatographic zone on which is disposed a plurality of microporous particles. The chromatographic zone can effectively reduce the "hook effect" in a simple, efficient, and relatively inexpensive manner. In particular, the plurality of microporous particles allows larger-sized analyte/probe complexes to reach the detection zone before the uncomplexed analyte. Because the uncomplexed analyte is substantially inhibited from competing with the complexes for the binding sites at the detection zone, the incidence of "false negatives" may be limited, even at relatively high analyte concentrations.

Referring to FIG. 1, for instance, one embodiment of a flow-through assay device 20 that can be formed according to the present invention will now be described in more detail. As shown, the device 20 contains a porous membrane 23 optionally supported by a rigid material 21. In general, the porous membrane 23 can be made from any of a variety of materials through which the test sample is capable of passing. For example, the materials used to form the porous membrane 23 can include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; nylon membranes; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyester sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The device 20 may also contain a wicking pad 28. The wicking pad 28 generally receives fluid that has migrated through the entire porous membrane 23. As is well known in the art, the wicking pad 28 can assist in promoting capillary action and fluid flow through the membrane 23.

To initiate the detection of an analyte within the test sample, a user may directly apply the test sample to a portion of the porous membrane 23 through which it can then travel. Alternatively, the test sample may first be applied to a sampling pad (not shown) that is in fluid communication with the porous membrane 23. Some suitable materials that can be used to form the sampling pad include, but are not limited to, nitrocellulose, cellulose, porous polyethylene pads, and glass fiber filter paper. If desired, the sampling pad may also contain one or more assay pretreatment reagents, either diffusively or non-diffusively attached thereto.

In the illustrated embodiment, the test sample travels from the sampling pad (not shown) to a conjugate pad 22 that is placed in communication with one end of the sampling pad. The conjugate pad 22 is formed from a material through which the test sample is capable of passing. For example, in one embodiment, the conjugate pad 22 is formed from glass fibers. Although only one conjugate pad 22 is shown, it should be understood that other conjugate pads may also be used in the present invention.

To facilitate accurate detection of the presence or absence of an analyte within the test sample, probes are applied at various locations of the device 20. As described in more detail below, probes may be used for both detection of the analyte and for calibration. Any substance generally capable of generating a signal that is detectable visually or by an instrumental device may be used as probes. Various suitable substances can include chromogens; catalysts; fluorescent compounds; chemiluminescent compounds; phosphorescent compounds; radioactive compounds; direct visual labels, including colloidal metallic (e.g., gold) and non-metallic particles, dye particles, enzymes or substrates, or organic polymer latex particles; liposomes or other vesicles containing signal producing substances; and the like. For instance, some enzymes suitable for use as probes are disclosed in U.S. Pat. No. 4,275,149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferylphosphate. Other suitable probes may be described in U.S. Pat. Nos. 5,670,381 to Jou, et al. and 5,252,459 to Tarcha, et al., which are incorporated herein in their entirety by reference thereto for all purposes.

In some embodiments, the probes can contain a fluorescent compound that produces a detectable signal. The fluorescent compounds can be fluorescent molecules, polymers, dendrimers, particles, and the like. Some examples of suitable fluorescent molecules, for instance, include, but are not limited to, fluorescein, europium chelates, phycobiliprotein, rhodamine and their derivatives and analogs. A visually detectable, colored compound can also be used as a probe, thereby providing for a direct colored readout of the presence or concentration of the analyte in the sample without the need for further signal producing reagents.

The probes, such as described above, may be used alone or in conjunction with a microparticle (sometimes referred to as "beads" or "microbeads"). For instance, naturally occurring microparticles, such as nuclei, mycoplasma, plasmids, plastids, mammalian cells (e.g., erythrocyte ghosts), unicellular microorganisms (e.g., bacteria), polysaccharides (e.g., agarose), and the like, can be used. Further, synthetic microparticles may also be utilized. For example, in one embodiment, latex microparticles that are labeled with a fluorescent or colored dye are utilized. Although any latex microparticle may be used in the present invention, the latex microparticles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and the like, or an aldehyde, carboxyl, amino, hydroxyl, or hydrazide derivative thereof. Other suitable microparticles may be described in U.S. Pat. Nos. 5,670,381 to Jou, et al. and 5,252,459 to Tarcha, et al., which are incorporated herein in their entirety by reference thereto for all purposes. Some commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. Commercially available examples of suitable colored, latex microparticles include carboxylated latex beads sold by Bang's Laboratory, Inc.

In some instances, it is desired to modify the probes in some manner so that they are more readily able to bond to the analyte. In such instances, the probes can be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members can include antigens, haptens, aptamers, antibodies, and complexes thereof, including those formed by recombinant DNA methods or peptide synthesis. An antibody can be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte.

Figure 2:
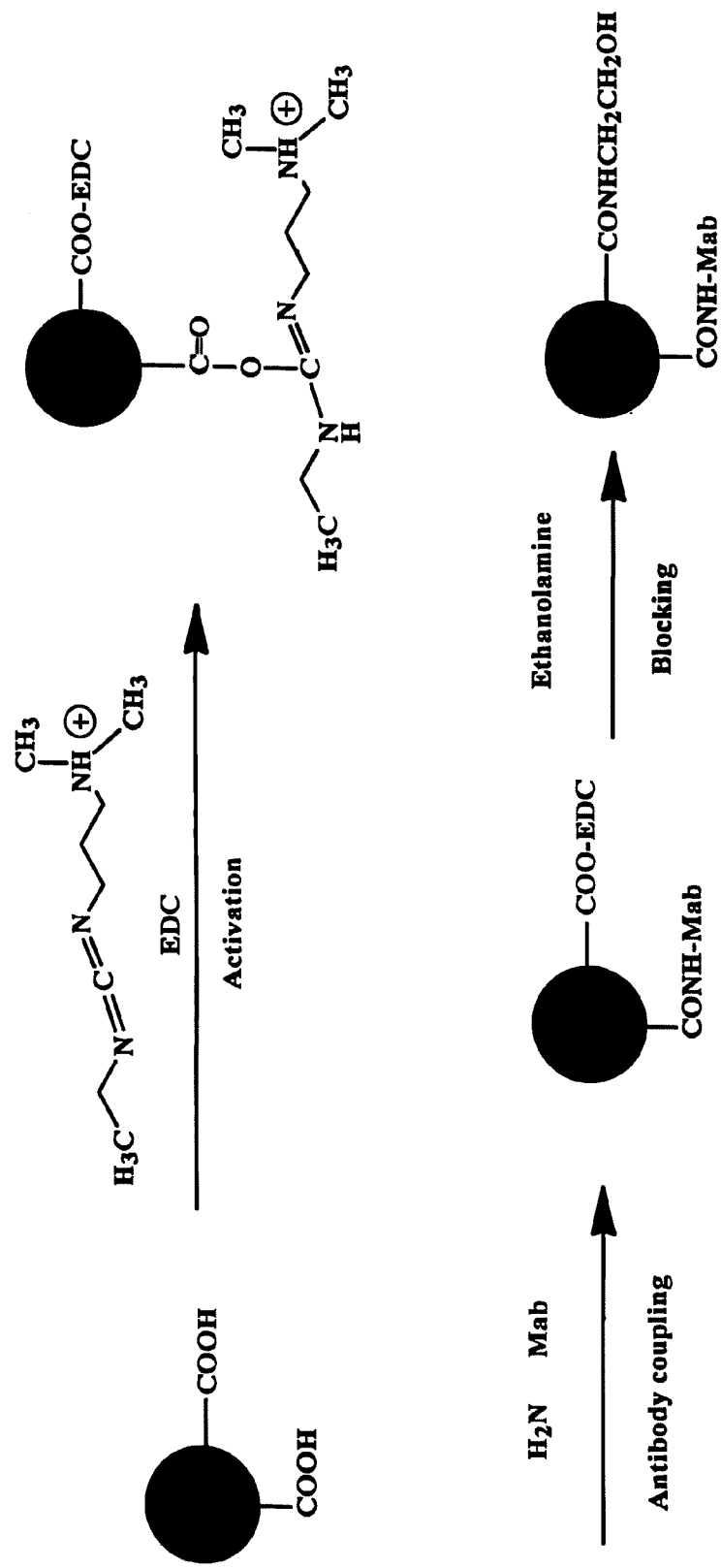
FIG. 2 is a graphical illustration of one embodiment for covalently conjugating an antibody to carboxylated nanoparticles.

The specific binding members can generally be attached to the probes using any of a variety of well-known techniques. For instance, covalent attachment of the specific binding members to the probes (e.g., microparticles) can be accomplished using carboxylic, amino, aldehyde, bromoacetyl, iodoacetyl, thiol, epoxy and other reactive or linking functional groups, as well as residual free radicals and radical cations, through which a protein coupling reaction can be accomplished. A surface functional group can also be incorporated as a functionalized co-monomer because the surface of the microparticle can contain a relatively high surface concentration of polar groups. In addition, although microparticle probes are often functionalized after synthesis, in certain cases, such as poly(thiophenol), the microparticles are capable of direct covalent linking with a protein without the need for further modification. For example, referring to FIG. 2, one embodiment of the present invention for covalently conjugating a probe is illustrated. As shown, the first step of conjugation is activation of carboxylic groups on the probe surface using carbodiimide. In the second step, the activated carboxylic acid groups are reacted with an amino group of an antibody to form an amide bond. The activation and/or antibody coupling can occur in a buffer, such as phosphate-buffered saline (PBS) (e.g., pH of 7.2) or 2-(N-morpholino) ethane sulfonic acid (MES) (e.g., pH of 5.3). As shown, the resulting probes can then be blocked with ethanolamine, for instance, to form the probe conjugate. Besides covalent bonding, other attachment techniques, such as physical adsorption, may also be utilized in the present invention.

Figure 3:
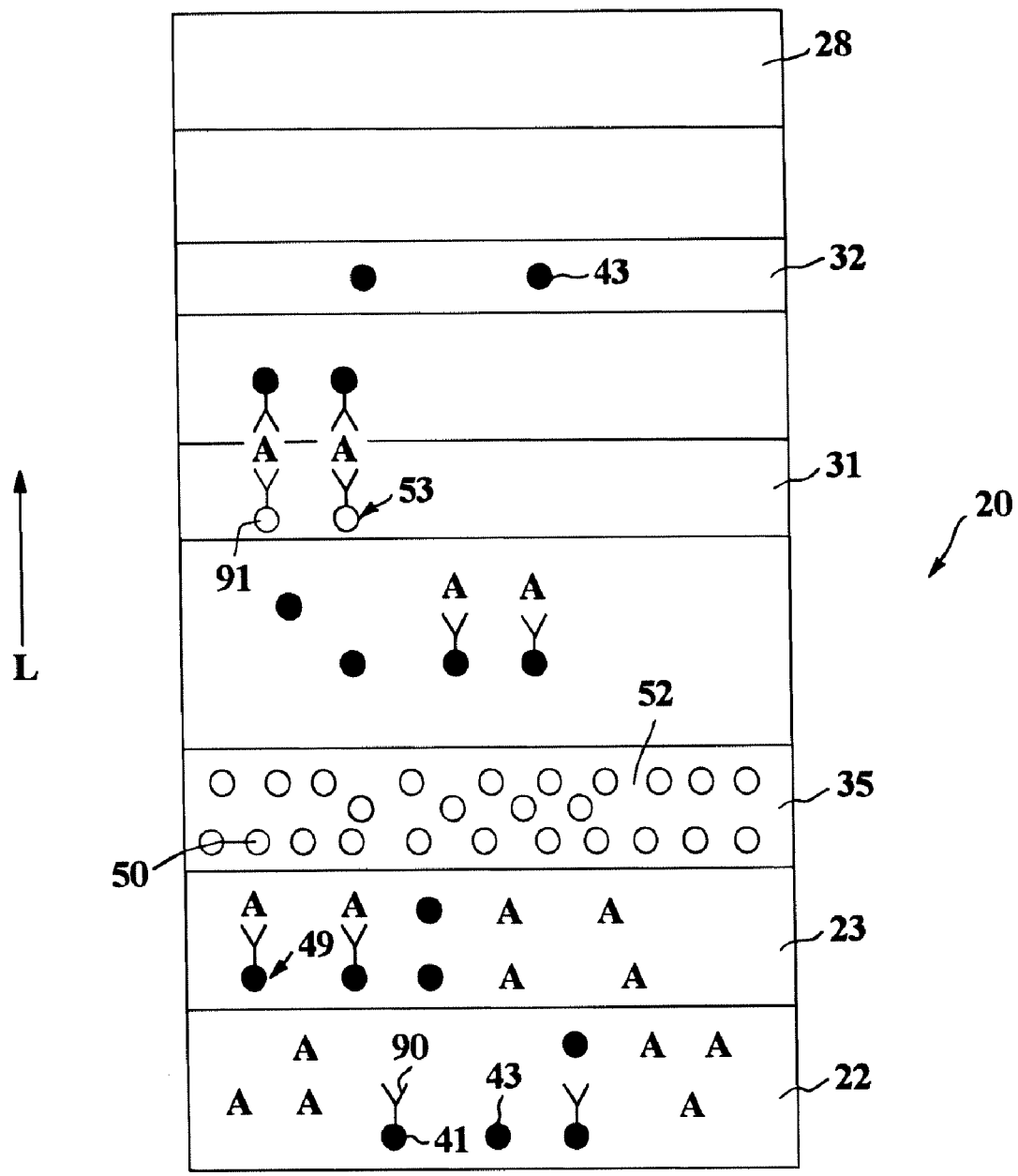
FIG. 3 is a schematic illustration of one embodiment of a flow-through assay device of the present invention, shown before the uncomplexed analyte travels through the chromatographic zone.
Figure 4:
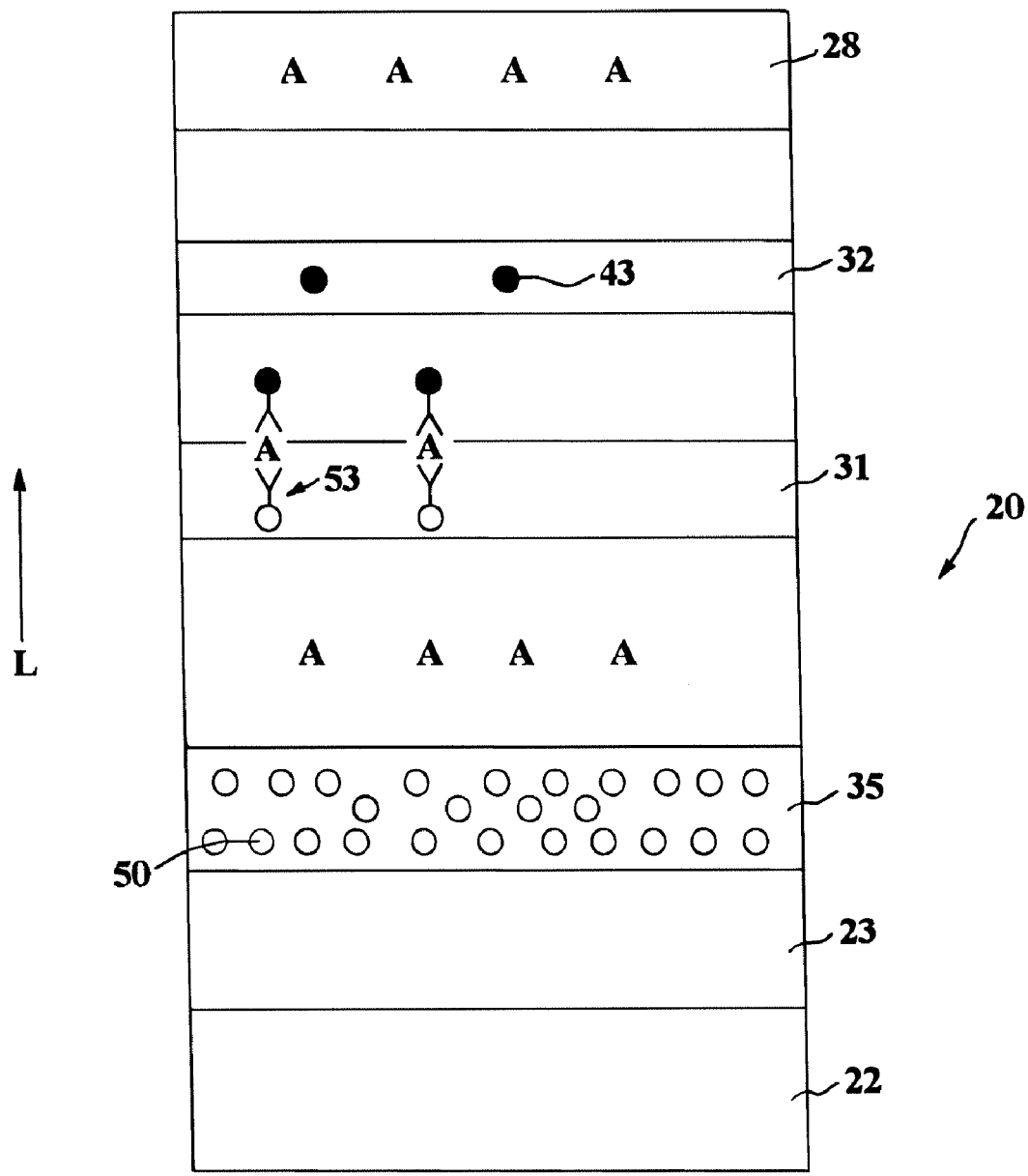
FIG. 4 is a schematic illustration of the embodiment of FIG. 3, shown after the uncomplexed analyte travels through the chromatographic zone.
Figure 5:
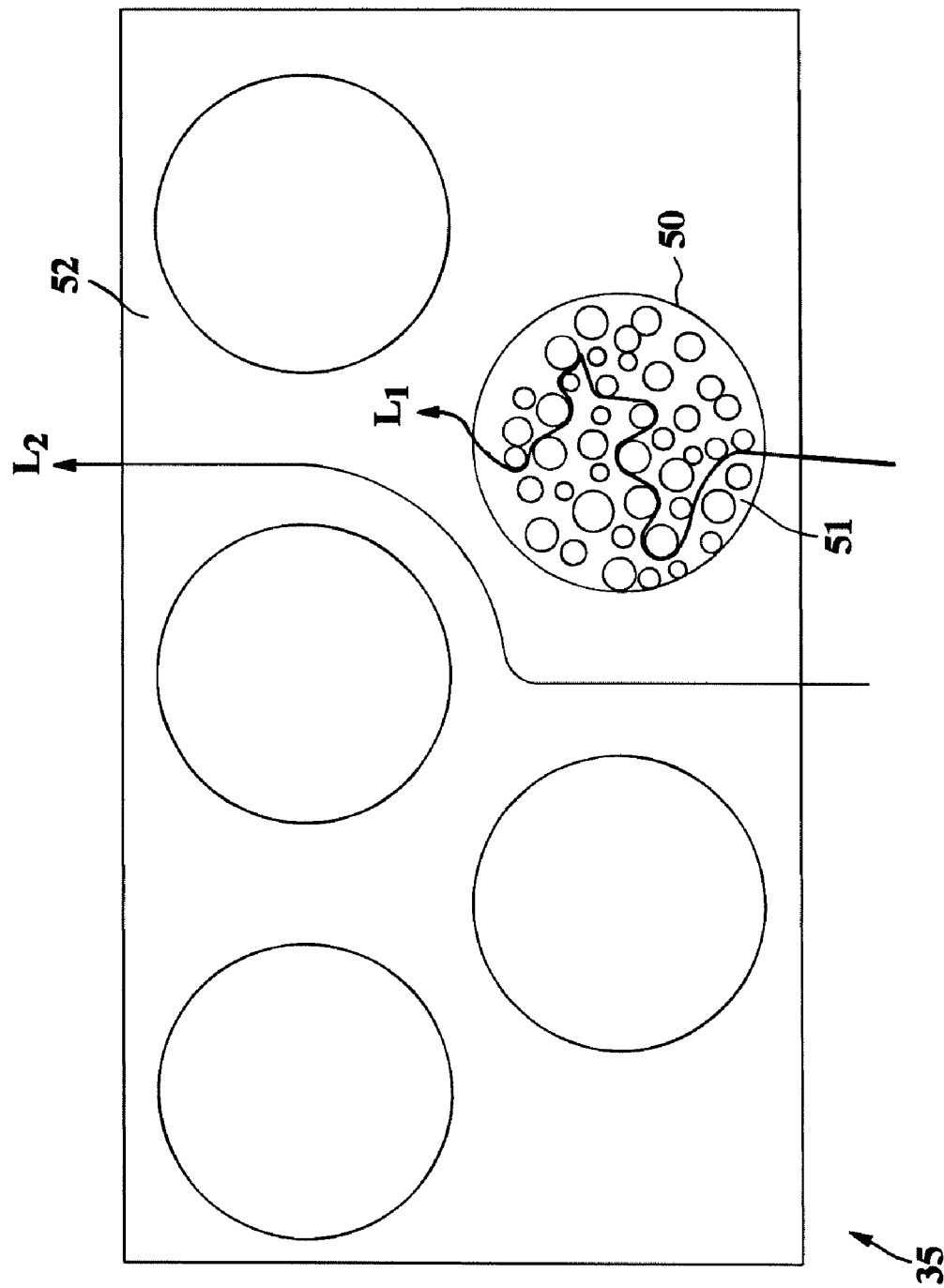
FIG. 5 is an exploded view of the chromatographic zone shown in FIG. 1.

As indicated above, some of the analyte in the test sample may not become complexed to the conjugated probes in the desired manner, particularly when the analyte is present in the test sample at high concentrations. This uncomplexed analyte can later compete with the complexed analyte for the capture reagent at the detection zone 31 (described below), thereby adversely affecting the accuracy of the assay device 20. To counteract this affect, the porous membrane 23 contains a chromatographic zone 35 on which a plurality of microporous particles 50 are distributed. As shown in FIGS. 3-5, the presence of microporous particles 50 allows the chromatographic zone 35 to act as a "gel permeation" column in that larger molecules move through the chromatographic zone 35 at a faster rate than smaller molecules. Specifically, as shown in FIG. 5, molecules larger in size than the micropores 51 of the microporous particles 50 cannot flow therethrough and thus are forced to flow through the spaces 52 between the particles 50, i.e., through the pores of the membrane 23 (illustrated as directional arrow L2). Because the micropores 51 of the particles 50 form "tortuous paths" (i.e., paths having complex shapes) within the particulate structure, it generally takes a longer period of time for a molecule to travel through the micropores 51 than through the spaces 52 between the particles 50. Accordingly, when traveling through the chromatographic zone 35, larger-sized molecules exit first. Intermediate-sized molecules penetrate the microporous particles 50 to varying extents depending on their size. Finally, very small molecules flow through the micropores 51 of the particles 50 (illustrated by directional arrow L1) and thus exit the chromatographic zone 35 last. Generally speaking, analyte/probe complexes are larger in size than uncomplexed analytes. Accordingly, the complexes can reach the detection zone 31 and bind to a capture reagent contained thereon before the uncomplexed analyte reaches the detection zone 31. In this manner, competition between the complexed and uncomplexed analyte is inhibited.

The chromatographic zone 35 generally provides a single distinct region (e.g., line, dot, etc.), although multiple regions are certainly contemplated by the present invention. For instance, in the illustrated embodiment, a single line is utilized. When utilized, the width of the line may generally vary. For example, in some embodiments, the width of the line in the direction L of analyte flow is from about 10% to about 100%, and in some embodiments, from about 10% to about 50% of the total distance measured from the location at which the analyte is applied (e.g., the conjugate pad 22) to the detection zone 31. Further, the line may be disposed in a direction that is substantially perpendicular to the flow of the test sample through the device 20. Likewise, in some embodiments, the line may be disposed in a direction that is substantially parallel to the flow of the test sample through the device 20.

The criteria for selecting appropriate microporous particles 50 for use in a given assay can include a variety of factors, such as the nature of the analyte of interest, the conditions of testing, the nature of the probes utilized, etc. Typically, it is desired that the microporous particles 50 have a relative uniform pore and particle size distribution and good mechanical and chemical stability. In addition, it is also typically desired that the surface of the microporous particles 50 remains chemically inert to other components of the assay device 20. For instance, the surface of the microporous particles 50 is generally chemically inert with respect to the analyte. Some examples of microporous particles 50 that may be used in the present invention include, but are not limited to, synthetic polymeric particles, such as polystyrenes (e.g., highly crosslinked polystyrene), polyacrylamides, polyacrylonitriles; silica beads, etc. Specific examples of some suitable synthetic microporous particles 50 are described, for instance, in U.S. Pat. No. 4,110,529 to Stoy; 4,940,734 to Ley, et al.; and 5,314,923 to Cooke, et al., which are incorporated herein in their entirety by reference thereto for all purposes. In embodiments in which the probes are also microporous particles, it should be understood that the microporous particles 50 of the chromatographic zone 35 may be the same as the probes.

The average diameter of the microporous particles 50 may generally vary as desired. For example, in some embodiments, the average diameter of the particles 50 can range from about 0.1 to about 1,000 microns, in some embodiments from about 0.1 to about 100 microns, and in some embodiments, from about 1 to about 10 microns. Typically, the particles 50 are substantially spherical in shape (i.e., beads), although other shapes including, but not limited to, plates, rods, bars, irregular shapes, etc., are suitable for use in the present invention. As will be appreciated by those skilled in the art, the composition, shape, size, and/or density of the particles 50 may widely vary.

Generally speaking, the micropores 51 of the particles 50 have an average size (i.e., diameter) that is smaller than the spaces between the particles 50 formed by the pores 52 of the porous membrane 23. Specifically, the average size of the micropores 51 is typically at least about 100%, in some embodiments, at least about 150%, and in some embodiments, at least about 250% smaller than the average size of the spaces therebetween. In some embodiments, for instance, the micropores 51 have an average size less than about 100 nanometers, in some embodiments from about 5 to about 100 nanometers, and in some embodiments, from about 10 to about 60 nanometers. As a comparison, the pores 52 of the porous membrane 23 typically have an average size of greater than about 200 nanometers, in some embodiments from about 200 to about 5000 nanometers, and in some embodiments, from about 200 to about 2500 nanometers.

The assay device 20 may also contain a detection zone 31, on which is immobilized a capture reagent that is capable of binding to the conjugated probes. For example, in some embodiments, the capture reagent may be a biological capture reagent. Such biological capture reagents are well known in the art and can include, but are not limited to, antigens, haptens, antibodies, protein A or G, avidin, streptavidin, secondary antibodies, and complexes thereof. In many cases, it is desired that these biological capture reagents are capable of binding to a specific binding member (e.g., antibody) present on the probes. In addition, it may also be desired to utilize various non-biological materials for the capture reagent. For instance, in some embodiments, the capture reagent can include a polyelectrolyte. The polyelectrolytes can have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydialiyldimethyl-ammonium chloride; cationic cellulose derivatives, such as cellulose copolymers or cellulose derivatives grafted with a quaternary ammonium water-soluble monomer; and the like. In one particular embodiment, CelQuat® SC-230M or H-100 (available from National Starch & Chemical, Inc.), which are cellulosic derivatives containing a quaternary ammonium water-soluble monomer, can be utilized. Moreover, some suitable examples of polyelectrolytes having a net negative charge include, but are not limited to, polyacrylic acids, such as poly(ethylene-co-methacrylic acid, sodium salt), and the like. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada.

The capture reagent serves as a stationary binding site for the analyte/probe complexes. Specifically, analytes, such as antibodies, antigens, etc., typically have two binding sites. Upon reaching the detection zone 31, one of these binding sites is occupied by the specific binding member of the conjugated probe. However, the free binding site of the analyte can bind to the immobilized capture reagent. Upon being bound to the immobilized capture reagent, the complexed probes form a new ternary sandwich complex.

The detection zone 31 may generally provide any number of distinct detection regions so that a user can better determine the concentration of a particular analyte within a test sample. Each region may contain the same capture reagents, or may contain different capture reagents for capturing multiple analytes. For example, the detection zone 31 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions can be disposed in the form of lines in a direction that is substantially parallel to the flow of the test sample through the assay device.

Although the detection zone 31 may indicate the presence of an analyte, it is often difficult to determine the relative concentration of the analyte within the test sample using solely a detection zone 31. Thus, the assay device 20 may also include a calibration zone 32. In this embodiment, the calibration zone 32 is formed on the porous membrane 23 and is positioned downstream from the detection zone 31. The calibration zone 32 is provided with a capture reagent that is capable of binding to any remaining uncaptured probes that pass through the length of the membrane 23. The capture reagent utilized in the calibration zone 32 may be the same or different than the capture reagent used in the detection zone 31. Moreover, similar to the detection zone 31, the calibration zone 32 may also provide any number of distinct calibration regions in any direction so that a user can better determine the concentration of a particular analyte within a test sample. Each region may contain the same capture reagents, or may contain different capture reagents for capturing different probes.

The calibration regions may be pre-loaded on the porous membrane 23 with different amounts of the capture reagent so that a different signal intensity is generated by each calibration region upon migration of the probes. The overall amount of binder within each calibration region can be varied by utilizing calibration regions of different sizes and/or by varying the concentration or volume of the capture reagent in each calibration region. If desired, an excess of probes can be employed in the assay device 20 so that each calibration region reaches its full and predetermined potential for signal intensity. That is, the amount of probes that are deposited upon calibration regions are predetermined because the amount of the capture reagent employed on the calibration regions is set at a predetermined and known level.

In general, a variety of flow-through assay devices may be constructed according to the present invention. In this regard, various embodiments of the present invention will now be described in more detail. It should be understood, however, that the embodiments discussed below are only exemplary, and that other embodiments are also contemplated by the present invention. For instance, referring to FIGS. 3-4, one particular embodiment in which probes 41 are used for detection and probes 43 are used for calibration is shown. In this embodiment, the detection probes 41 and calibration probes 43 are applied to the conjugate pad 22 and are thus capable of flowing through the device 20 (as indicated by the directional arrow L) when placed in communication with the test sample. The detection probes 41 are conjugated with a specific binding member 90 for an analyte A so that, upon contact with the analyte A, the probes 41 bind thereto to form analyte/probe complexes 49.

As shown in FIG. 3, the probe/analyte complexes 49, any free analyte A, and the calibration probes 43 flow from the conjugate pad 22 through the porous membrane 23 until they reach the chromatographic zone 35 on which is disposed a plurality of microporous particles 50. The larger complexes 49 and calibration probes 43 readily flow through the spaces 52 between the particles 50, while the smaller uncomplexed analyte A flows within the micropores of the particles 50 at a slower rate. The analyte/probe complexes 49 then flow through the device 20 until they reach the detection zone 31 where they bind to a capture reagent 91, such as an antibody, to form sandwich complexes 53. Further, the calibration probes 43 flow to the calibration zone 32 and bind to a capture reagent (not shown), such as polyelectrolyte. Thereafter, as shown in FIG. 4, the uncomplexed analyte A travels through the chromatographic zone 35 to reach the detection zone 31. Because the complexes 49 are already bound to the capture reagent, however, the analyte A moves through the detection zone 31 and calibration zone 32 until it reaches the wicking pad 28. Thus, at the detection zone 31, the amount of the analyte can be ascertained from the signal intensity of the detection probes 41. If desired, this signal intensity may be calibrated by the signal intensity of the calibration probes 43 at the calibration zone 32. The signal intensities may be measured visually or through the aid of a device, such as a fluorescence reader.

Although various embodiments of device configurations have been described above, it should be understood, that a device of the present invention may generally have any configuration desired, and need not contain all of the components described above. Various other device configurations and/or assay formats, for instance, are described in U.S. Pat. Nos. 5,395,754 to Lambotte, et al.; 5,670,381 to Jou, et al.; and 6,194,220 to Malick, et al., which are incorporated herein in their entirety by reference thereto for all purposes.

The present inventors have discovered that the presence of a chromatographic zone on the porous membrane of an assay device can effectively reduce the "hook effect" in a simple, efficient, and relatively inexpensive manner. In particular, a plurality of microporous particles can be disposed on the chromatographic zone to allow larger-sized analyte/probes complexes to reach the detection before any uncomplexed analyte. Accordingly, the uncomplexed analyte does not compete with the complexes for available binding sites at the detection zone. Because the uncomplexed analyte is inhibited from occupying a substantial number of the binding sites at the detection zone, the incidence of "false negatives" may be limited, even at relatively high analyte concentrations.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for detecting the presence or quantity of an analyte residing in a test sample, said method comprising:
   i) providing a flow-through assay device comprising a porous membrane, said porous membrane being in communication with conjugated detection probes capable of generating a detection signal, said porous membrane defining a chromatographic zone within which a plurality of particles having micropores are immobilized and a detection zone located downstream from said chromatographic zone, wherein a capture reagent is immobilized within said detection zone;
   ii) contacting a test sample containing the analyte with said conjugated detection probes so that analyte/probe complexes and uncomplexed analyte are formed;
   iii) allowing said analyte/probe complexes and said uncomplexed analyte to reach said chromatographic zone and then said detection zone, wherein said analyte/probe complexes move through said chromatographic zone at a faster rate than said uncomplexed analyte such that said analyte/probe complexes reach said detection zone before said uncomplexed analyte; and
   iv) detecting said detection signal generated by said detection probes within said detection zone.

2. The method of claim 1, wherein said particles define a plurality of spaces therebetween, said spaces having an average size that is greater than the average size of the micropores of said particles.

3. The method of claim 2, wherein the average size of said micropores is at least about 100% less than the average size of said spaces.

4. The method of claim 2, wherein the average size of said micropores is at least about 150% less than the average size of said spaces.

5. The method of claim 2, wherein the average size of said micropores is at least about 100% less than the average size of said spaces.

6. The method of claim 1, wherein said particles are formed from polystyrenes, polyacrylamides, polyacrylonitriles, silica beads, or combinations thereof.

7. The method of claim 1, wherein the surface of said particles is chemically inert to the analyte.

8. The method of claim 1, further comprising measuring the intensity of the detection signal generated within said detection zone.

9. The method of claim 1, wherein said porous membrane further comprises a calibration zone a capable of generating a calibration signal, wherein the amount of the analyte within the test sample is determined from said detection signal as calibrated by said calibration signal.

10. The method of claim 9, wherein said porous membrane is in communication with calibration probes, said calibration probes generating said calibration signal when present within said calibration zone.

11. The method of claim 10, further comprising generating a calibration curve by plotting the intensity of the detection signal calibrated by the intensity of the calibration signal for a plurality of predetermined analyte concentrations.

12. The method of claim 1, wherein said particles have an average diameter of from about 0.1 to about 100 microns.

13. The method of claim 1, wherein said particles have an average diameter of from about 1 to about 10 microns.

14. The method of claim 1, wherein said porous membrane contains pores having an average size of greater than about 200 nanometers.

15. The method of claim 1, wherein said porous membrane contains pores having an average size of from about 200 to about 5000 nanometers.

16. The method of claim 1, wherein said porous membrane contains pores having an average size of from about 200 to about 2500 nanometers.

17. The method of claim 1, wherein the detections probes are conjugated with an antibody.

18. The method of claim 1, wherein the capture reagent is an antibody.

19. The method of claim 1, wherein the micropores have an average size less than about 100 nanometers.

20. The method of claim 1, wherein the micropores have an average size from about 5 to about 100 nanometers.

21. The method of claim 1, wherein the micropores have an average size from about 10 to about 60 nanometers.

* * * * *